(12) United States Patent
Duc

(10) Patent No.: US 7,956,231 B2
(45) Date of Patent: Jun. 7, 2011

(54) METHOD FOR SEPARATION OF OLEFINS

(75) Inventor: Tuat Pham Duc, Penzberg (DE)

(73) Assignee: Linde Aktiengesellschaft, Wiesbaden (DE)

( * ) Notice: Subject to any disclaimer, the term of this patent is extended or adjusted under 35 U.S.C. 154(b) by 1096 days.

(21) Appl. No.: 11/714,278

(22) Filed: Mar. 6, 2007

(65) Prior Publication Data

US 2007/0219401 A1    Sep. 20, 2007

(30) Foreign Application Priority Data

Mar. 7, 2006 (DE) .......................... 10 2006 010 519

(51) Int. Cl.
*C07C 7/00* (2006.01)

(52) U.S. Cl. ........ 585/809; 585/639; 585/802; 585/807; 208/351

(58) Field of Classification Search .................... None
See application file for complete search history.

(56) References Cited

U.S. PATENT DOCUMENTS

| | | | | |
|---|---|---|---|---|
| 2,219,529 A * | 10/1940 | Pyzel | ............................ | 208/228 |
| 3,113,164 A * | 12/1963 | Mathis et al. | ................. | 585/628 |
| 3,284,339 A * | 11/1966 | Begley et al. | ................. | 585/633 |
| 3,349,147 A * | 10/1967 | Clay et al. | ..................... | 585/628 |
| 3,711,569 A * | 1/1973 | Tschopp et al. | ............. | 585/655 |
| 4,695,662 A * | 9/1987 | Vora | ............................... | 585/324 |
| 4,868,342 A * | 9/1989 | Verson | ........................... | 568/697 |
| 5,110,446 A * | 5/1992 | Harandi et al. | ............... | 208/100 |
| 5,960,643 A * | 10/1999 | Kuechler et al. | ................ | 62/620 |
| 6,790,342 B1 * | 9/2004 | Porter et al. | ..................... | 208/49 |
| 7,268,265 B1 * | 9/2007 | Stewart et al. | ................ | 585/324 |
| 2001/0044565 A1 * | 11/2001 | Keady et al. | .................... | 585/809 |
| 2002/0004622 A1 * | 1/2002 | Dai et al. | ....................... | 585/260 |
| 2004/0211703 A1 * | 10/2004 | Duhon et al. | .................. | 208/106 |
| 2005/0101815 A1 * | 5/2005 | Xu et al. | ........................ | 585/639 |
| 2005/0101816 A1 * | 5/2005 | Xu et al. | ........................ | 585/639 |

FOREIGN PATENT DOCUMENTS

| EP | 0 683 146 A1 | 11/1995 |
|---|---|---|
| EP | 1 378 559 A | 1/2004 |

* cited by examiner

*Primary Examiner* — Tam M Nguyen
(74) *Attorney, Agent, or Firm* — Millen, White, Zelano & Branigan, P.C.

(57) ABSTRACT

To decrease capital costs of crack gas treatment of the olefin plant, a method for separation of olefins reduces the units for catalytic hydrogenation. In the method, olefins having three carbon atoms are separated from olefins having four carbon atoms. Crude gas is precompressed (1), precooled and dried (2), and passed into a C3/C4 separation stage (6) comprising a C4 absorber, operating at full crude gas pressure, and a depropanizer, operated at a pressure of 8 to 12 bar. In the C3/C4 separation stage, the olefins are separated into a fraction having at most three carbon atoms (C3−), and a fraction having at least four carbon atoms (C4+). The fraction having at most three carbon atoms is completely compressed (1) and passed to the catalytic hydrogenation (4); the fraction having at least four carbon atoms is passed out for further processing (7). The catalytic hydrogenation (4) yields a fraction having at least two carbon atoms (C2−), which is passed on to the low-temperature separation, and a fraction having three carbon atoms (C3), is passed to further processing (8).

2 Claims, 4 Drawing Sheets

METHOD FOR SEPARATION OF OLEFINS

The invention relates to a method for separation of olefins having three or four carbon atoms in a fractionation stage of a plant for production of olefins from hydrocarbonaceous feed (olefin plant), the longer-chain olefins of the hydrocarbonaceous feed being converted into a gas mixture of shorter-chain olefin products (crude gas) which is compressed and dried.

Olefins can be produced, for example, by thermal cracking in a cracking furnace (steam cracker) from long-chain hydrocarbons. The olefin gas generated in the cracking furnace (crude gas) is, after cooling and drying, fractionated into the various olefin fractions. According to the prior art, the separation sequence begins either with a fractionation stage in which olefins having at most two carbon atoms are separated from olefins having at least three carbon atoms (C2/C3 separation), or a fractionation stage in which olefins having at most three carbon atoms are separated from olefins having at least four carbon atoms (C3/C4 separation).

If the separation sequence begins with a C2/C3 separation, the resultant olefin fraction having at most two carbon atoms is passed, downstream of a catalytic hydrogenation, to the low-temperature part. The olefin fraction having at least three carbon atoms is separated in a depropanizer into a fraction having three carbon atoms and a fraction having at least four carbon atoms. The resultant fraction having three carbon atoms is subsequently likewise catalytically hydrogenated before its further processing.

If the separation sequence begins with a C3/C4 separation, according to the prior art, at crude gas pressure, an olefin fraction having at most three carbon atoms, and an olefin fraction having at least three carbon atoms are obtained. A sharp separation into a fraction having at most three carbon atoms and a fraction having at least four carbon atoms is not possible at the full crude gas pressure. For this the temperature would have to be increased to the extent that increased polymer formation and therefore undesirable deposit formation would occur. The fraction having at most three carbon atoms is fed, downstream of a catalytic hydrogenation, to a C2/C3 separation. The fraction having at least three carbon atoms is separated into a fraction having three carbon atoms and a fraction having at least four carbon atoms. The resultant olefin fraction having three carbon atoms must subsequently be likewise catalytically hydrogenated.

Therefore, in both cases two independent catalytic hydrogenation stages are required together with the corresponding fixed-bed reactors and methanol evaporator cooling for temperature setting in exothermic heat of reaction of the catalytic hydrogenation. The two reactors for the catalytic hydrogenation with their high-performance heat exchangers considerably burden the scope of equipment and thus the capital costs.

SUMMARY OF THE INVENTION

Thus, one aspect of the present invention is to decrease the capital costs of crack gas treatment of the olefin plant.

Upon further study of the specification and appended claims, further objects, aspects and advantages of this invention will become apparent to those skilled in the art.

The invention involves the use of a C3/C4 separation stage the comprises an absorber (C4 absorber), operated at full crude gas pressure (, and a separation column for separating olefins having at most three carbon atoms and olefins having at least four carbon atoms (depropanizer). The depropanizer is operated at a pressure of about 8 bar-12 bar. As a result, a catalytic hydrogenation having a corresponding fixed-bed reactor can be omitted.

As noted above, the C3/C4 separation stage operates at full crude gas pressure (i.e., the crude gas is sent to the C3/C4 separation stage without pressure reduction). Typically, the pressure of the crude gas is controlled by a compressor upstream of the C3/C4 separation stage. For example, the crude gas can be pressurized in a compressor having five compression stages.

Conventionally, in olefin plants according to the above-described prior art, either a separate catalytic hydrogenation of the fraction having at most two carbon atoms and of the fraction having three carbon atoms occurs, or separate catalytic hydrogenation of the fraction having at most three carbon atoms and of the fraction having three carbon atoms occurs.

The basic concept of the invention is to replace the two separate catalytic hydrogenations by one catalytic hydrogenation of the entire fraction having at most three carbon atoms. The entire fraction of the olefins having at most three carbon atoms is generated by the C3/C4 separation stage comprising the C4 absorber, operating at full crude gas pressure, and the depropanizer operating at a pressure of about 8-12 bar.

According to a particularly preferred embodiment of the invention, the hydrocarbonaceous gas (crude gas) generated in the olefin plant is delivered at full crude gas pressure into the C3/C4 separation stage comprising a C4 absorber operating at full crude gas pressure and a depropanizer operating at a pressure of about 8-12 bar and is separated into a fraction having at most three carbon atoms and a fraction having at least four carbon atoms. The pressure of the C4 absorber is set according to the invention by the corresponding pressure stages of the crude gas compression stage and is preferably about 15-39 bar, preferably about 15-23 bar. For example, a five stage compressor can be used in which in the fourth stage pressurizes the crude gas to 15-23 bar and the fifth stage pressurizes the crude gas to 30-39 bar. If the crude gas is sent to the C3/C4 separation stage after the fourth compressor stage, then the pressure can be about 15-23 bar. Alternatively, If the crude gas is sent to the C3/C4 separation stage after the fifth compressor stage, then the pressure can be about 30-39 bar. Advantageously, the entire fraction having at most three carbon atoms is fed to the next-highest stage of the crude gas compressor and subsequently passed on to the catalytic hydrogenation.

By means of the invention it is possible, in particular, to minimize the capital costs by the omission of a catalytic hydrogenation.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE DRAWINGS

Figure 1:
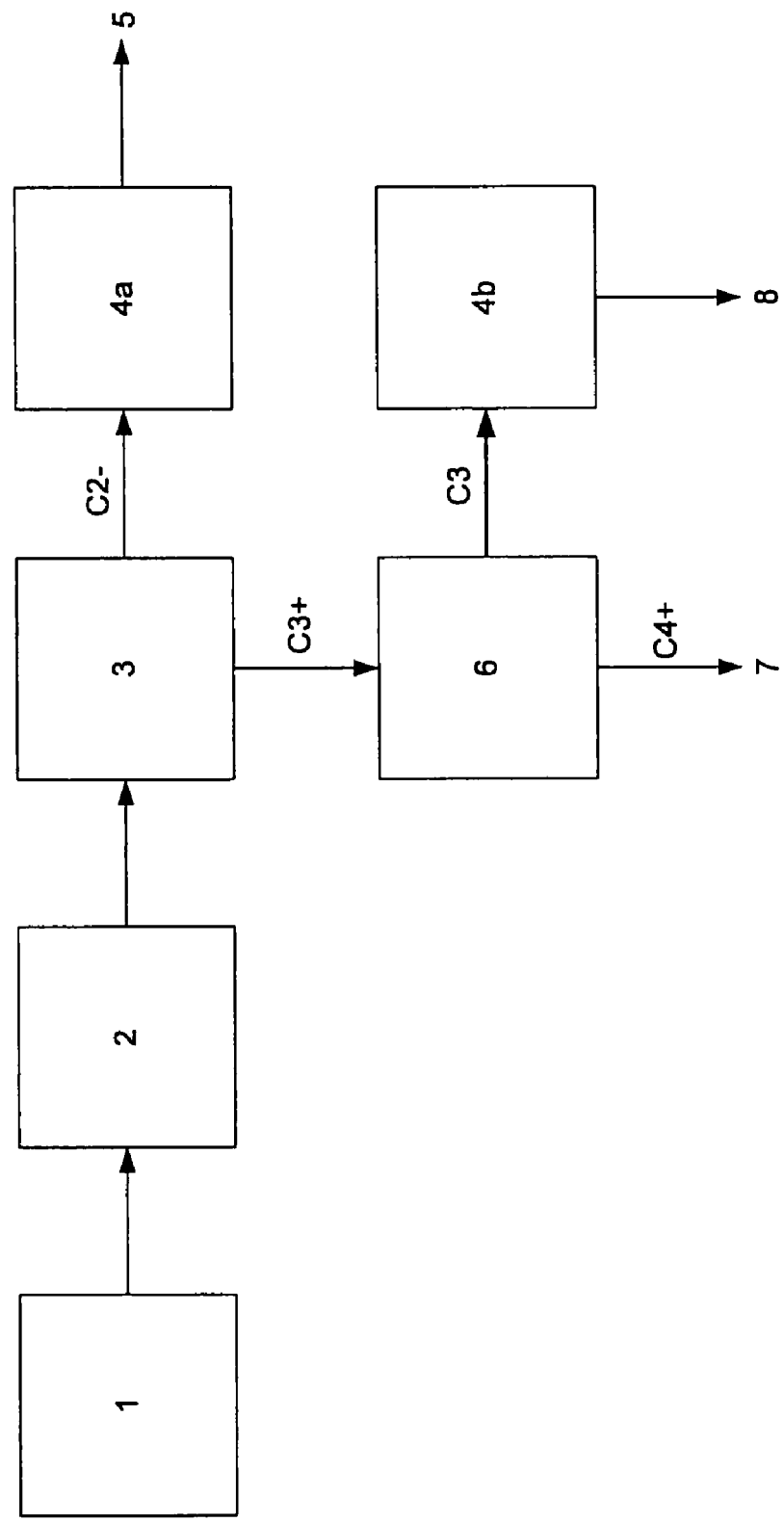
FIG. 1 shows a flow chart of a separation sequence starting with a C2/C3 separation according to the prior art.

The separation sequence of the prior art shown in FIG. 1 starts with the crude gas compression (1) with subsequent precooling and drying (2). The precooled and dried crude gas is separated in a C2/C3 separation (3) into olefins having at most two carbon atoms (C2−) and olefins having at least three carbon atoms (C3+). The olefin fraction having at most two carbon atoms is catalytically hydrogenated (4a) and passed onto the low-temperature part (5). The olefin fraction having at least three carbon atoms (C3+) is separated with pressure reduction in a C3/C4 separation (6) into a fraction having three carbon atoms (C3) and a fraction having at least four carbon atoms (C4+). The olefin fraction having four carbon atoms is supplied to further processing (7), while the fraction having three carbon atoms (C3) is catalytically hydrogenated in a second reactor (4b) and passed out (8).

Figure 2:
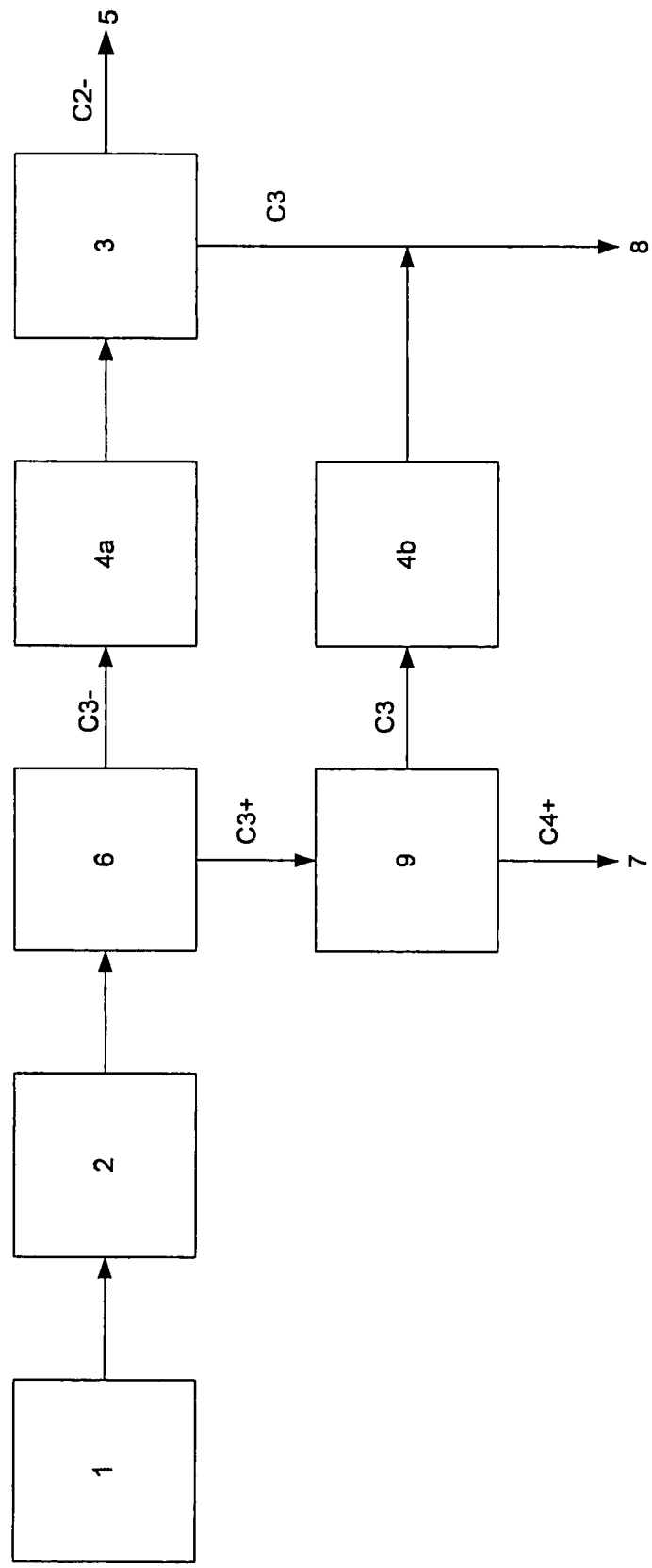
FIG. 2 shows a flow chart of a separation sequence starting with a C3/C4 separation according to the prior art.

FIG. 2 shows a variant of the prior art in which the precooled, dried and compressed crude gas (1, 2) is passed into a C3/C4 separation (6) where the olefins are separated into a fraction having at least three carbon atoms (C3+) and a fraction having at most three carbon atoms (C3−). The fraction having at least three carbon atoms is passed to a fractionation stage (9) which separates olefins having at most three carbon atoms from olefins having at least four carbon atoms. This produces a fraction having three carbon atoms (C3) and a fraction having at least four carbon atoms (C4+) which is passed out for further processing (7). The resultant fraction having three carbon atoms is catalytically hydrogenated (4b) and passed out (8). The fraction having at most three carbon atoms (C3−) is catalytically hydrogenated in a reactor (4a). From there the olefin fraction having at most three carbon atoms is passed into a C2/C3 separation (3) and separated into a fraction having at most two carbon atoms and a fraction having three carbon atoms. The olefin fraction having at most two carbon atoms is passed onto the low-temperature part (5), while the fraction having three carbon atoms is passed out (8) for further processing.

Figure 3:
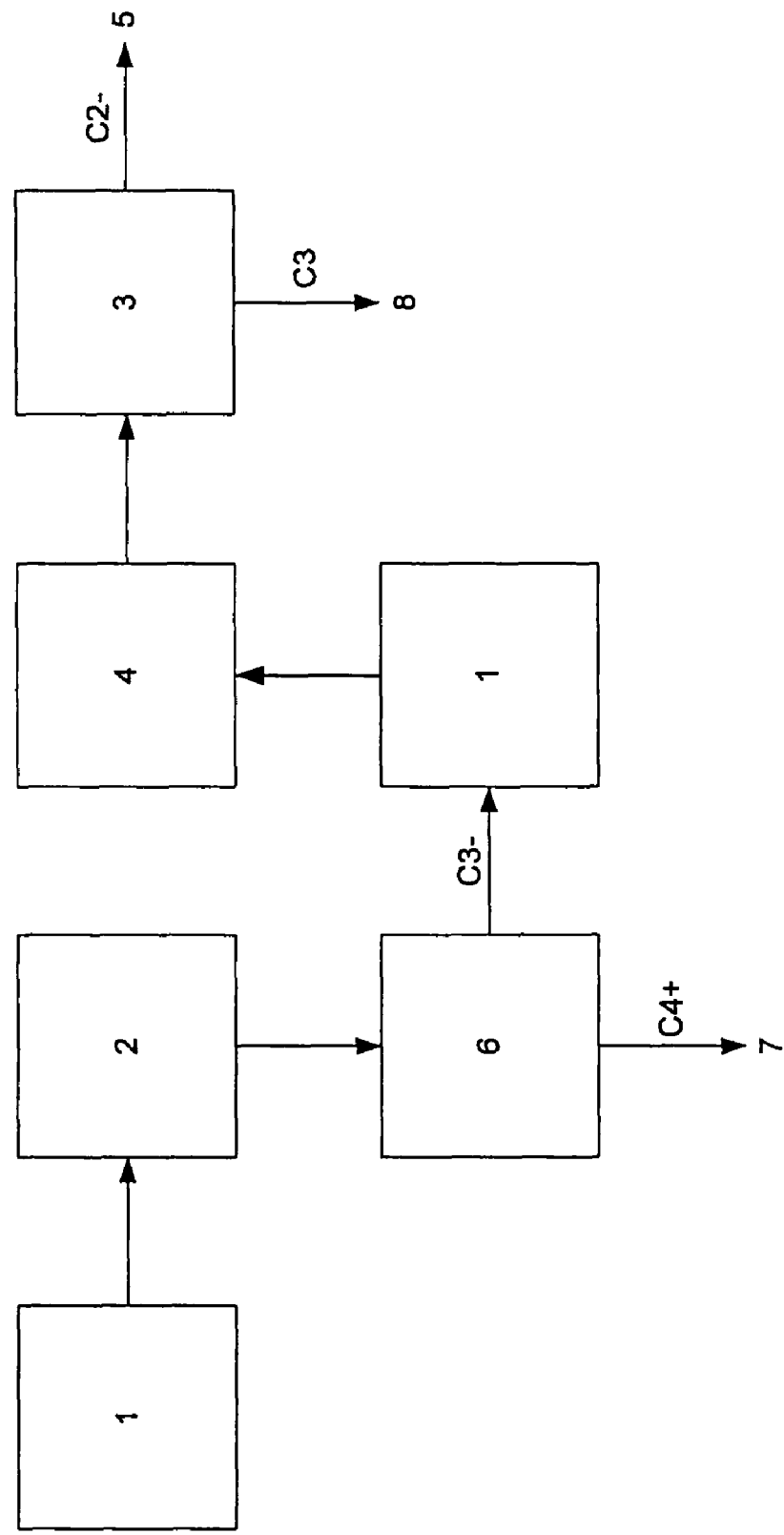
FIG. 3 shows a flow chart of the separation sequence according to the invention starting with a C3/C4 separation comprising a C4 absorber and a depropanizer.

FIG. 3 shows an embodiment of the invention. The crude gas is precompressed (1), precooled and dried (2). For example, precooling can be performed in a heat exchanger and drying can be performed using a molecular sieve adsorber. The first compressor 1 pressurizes the crude gas to a pressure of, for example, 15-23 bar. The crude gas is then passed into a C3/C4 separation (6) which comprises a C4 absorber operating at full crude gas pressure and a depropanizer which is operated at a pressure of 8 to 12 bar. There, the olefins are separated into a fraction having at most three carbon atoms (C3−) and a fraction having at least four carbon atoms (C4+). The fraction having at most three carbon atoms is completely compressed (1) and passed to the catalytic hydrogenation (4) (for example using a palladium based catalyst), while the fraction having at least four carbon atoms is passed out (7) for further processing. The fraction having at most three carbon atoms is separated downstream of the catalytic hydrogenation (4) in a C2/C3 separation (3) into a fraction having at least two carbon atoms (C2−) which is passed on to the low-temperature separation part (5) and a fraction having three carbon atoms (C3). For example, the low-temperature separation for the C2− fraction can comprise cooling the C2− fraction in the three stages while removing hydrogen and methane. The resultant C2 condensate can be sent to a demethanizer to remove the remaining methane and the C2 stream cane then be sent to a C2 splitter to separate ethene and ethane. The fraction having three carbon atoms is then passed to further processing (8). For example, the fraction having three carbon atoms can be subjected to hydrogenation and then sent to a C3 splitter to separate propene and propane.

Figure 4:
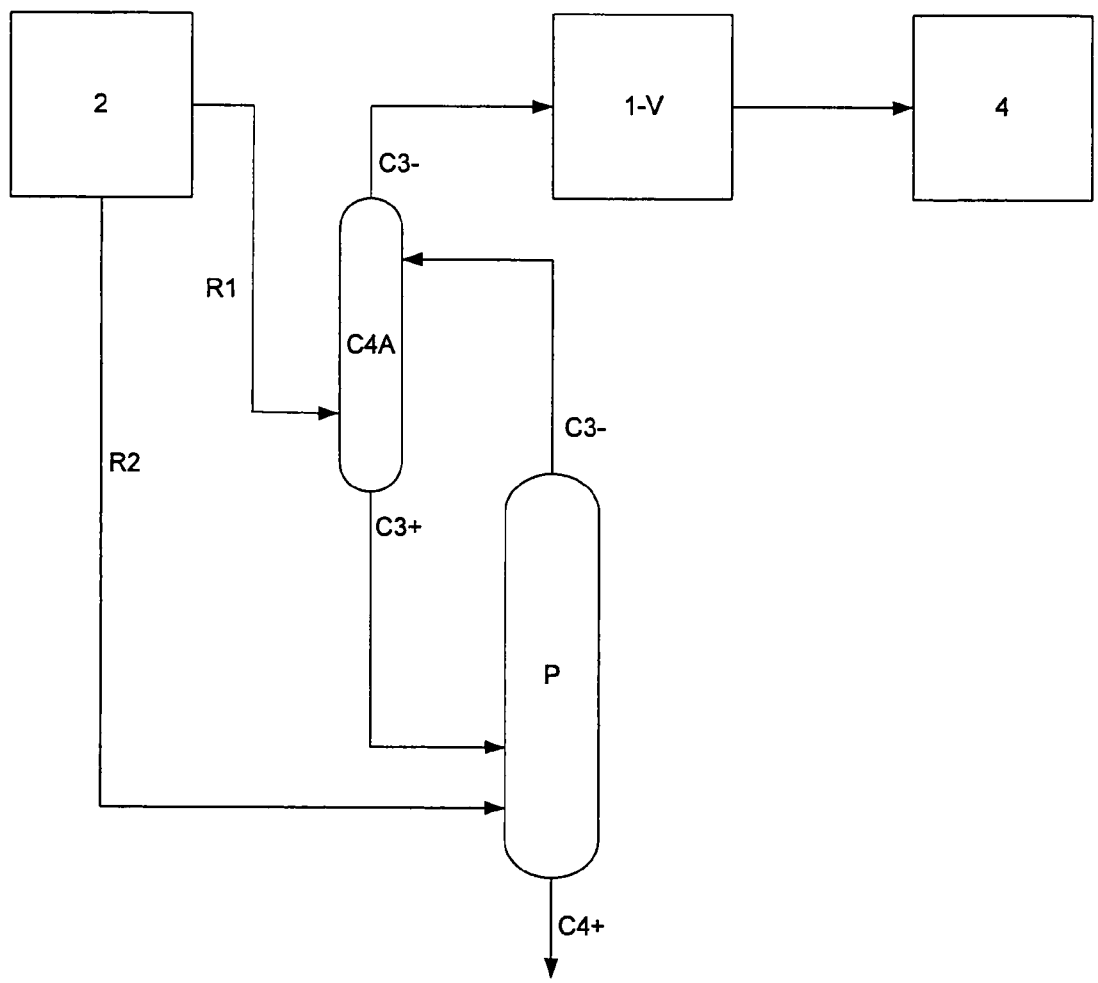
FIG. 4 shows a flow chart of the C4 absorber and the depropanizer

FIG. 4 shows, in one embodiment of the invention, the C3/C4 separation in detail with precooling and drying of the crude gas (2). One part of the crude gas (R1) (e.g., 70-90 vol. %) of the crude gas) is passed to the C4 absorber (C4A) and a second part of the crude gas (R2) (e.g., 10-30 vol. %) is passed directly to the depropanizer (P). At the C4 absorber (C4A) a fraction having at least three carbon atoms (C3+) is produced, at full crude gas pressure, and another fraction having at most three carbon atoms (C3−) is also produced. In the depropanizer, which operates at a pressure of 8 to 12 bar, a fraction having at most three carbon atoms (C3−) and a fraction having at least four carbon atoms (C4+) are produced. By recycling between C4 absorber (C4A) and depropanizer (P), the crude gas can be completely separated into a fraction having at most three carbon atoms (C3−) and a fraction having at least four carbon atoms (C4+). The fraction having at most three carbon atoms (C3−) is then passed to the catalytic hydrogenation (4) via the last stage of the compression (1-V).

The entire disclosures of all applications, patents and publications, cited herein and of corresponding German application No. DE 102006010519.2, filed Mar. 7, 2006, are incorporated by reference herein.

The preceding examples can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for separation of olefins having three carbon atoms from olefins having four carbon atoms, said method comprising:

introducing a crude hydrocarbonaceous feed gas containing olefins into a C3/C4 separation stage, operated at crude gas pressure, and a depropanizer separation column (P) separating olefins having at most three carbon atoms and olefins having at least four carbon atoms, said depropanizer (P) operating at a pressure of 8-12 bar, said crude hydrocarbonaceous feed gas is compressed, precooled, and dried prior to being introduced into said C3/C4 separation stage, and wherein, after being precooled and dried, a part (R1) of said crude gas is introduced into an absorber (C4A) and another part (R2) of said crude gas is introduced directly into said depropanizer (P), said C4 absorber produces a fraction having at least three carbon atoms (C3+), and another fraction having at most three carbon atoms (C3−), said depropanizer produces a fraction having at most three carbon atoms (C3−) and another fraction having at least four carbon atoms (C4+), at least a portion of said fraction having at most three carbon atoms (C3−) from said absorber is introduced into said depropanizer (P), and at least a portion of said fraction having at most three carbon atoms (C3−) from said depropanizer is recycled to said C4 absorber.

2. A method according to claim 1, wherein at least a portion of said fraction having at most three carbon atoms (C3−) from said absorber is compressed and then introduced into a catalytic hydrogenation (4) stage.

* * * * *